United States Patent [19]

Sarfatti

[11] 4,165,562

[45] Aug. 28, 1979

[54] PRECISION ENDODONTIC FILE

[76] Inventor: David E. Sarfatti, 1520 Spruce St., Apt. 907, Philadelphia, Pa. 19102

[21] Appl. No.: 824,158

[22] Filed: Aug. 12, 1977

[51] Int. Cl.$^2$ .............................................. A61C 5/02
[52] U.S. Cl. .................................................... 32/57
[58] Field of Search ................ 32/57, 40 R; 128/215, 128/218 N, 221, 329, 329 A

[56] References Cited

U.S. PATENT DOCUMENTS

| | | | |
|---|---|---|---|
| 3,380,489 | 4/1968 | Harautuneian | 128/215 |
| 3,562,913 | 2/1971 | Saffro | 32/57 |
| 3,703,767 | 11/1972 | Masseran | 32/57 |
| 3,713,221 | 1/1973 | Malmin | 32/57 |
| 3,772,791 | 11/1973 | Malmin | 32/57 |
| 3,781,996 | 1/1974 | Saffro | 32/57 |
| 3,855,705 | 12/1974 | Malmin | 32/57 |
| 3,889,673 | 6/1975 | Dovey | 128/215 |
| 3,905,375 | 9/1975 | Toyama | 128/329 A |
| 3,924,334 | 12/1975 | Lentine et al. | 32/57 |
| 3,961,422 | 1/1976 | Riitano et al. | 32/57 |
| 4,028,810 | 6/1977 | Vice | 32/57 |

*Primary Examiner*—Louis G. Mancene
*Assistant Examiner*—John J. Wilson
*Attorney, Agent, or Firm*—Steele, Gould & Fried

[57] ABSTRACT

A precision endodontic file including a threaded base having an endodontic file projecting outwardly therefrom is disclosed. A threaded sleeve threadedly receives the base to facilitate precise longitudinal adjustment of the file relative to the sleeve. The bottom end of the sleeve is utilized as a stop which abuts the tooth to thereby limit the depth of file penetration. The threaded body incorporates at least one lock which is continuously biased to a locking position. The threaded sleeve is provided with one or more slots into which the lock can extend to prevent the threaded body from turning relative to the sleeve once the desired length adjustment has been preset. A plastic, transparent throw away type cap overfits the combination of the file and the sleeve and is imprinted with a plurality of graduations thereon to indicate the distance that the bottom of the file extends from the bottom of the sleeve. By measuring precisely the depth of desired penetration from an x-ray, the length can be precisely set on the instrument by turning the body relative to the sleeve until the bottom of the file aligns with the proper graduation on the cap. The plastic cap is then removed from the sleeve and discarded to expose the working portions of the instrument. The cap acts to preserve sterility of the file prior to use and also to protect the file against accidental damage.

21 Claims, 5 Drawing Figures

U.S. Patent   Aug. 28, 1979   Sheet 2 of 2   4,165,562
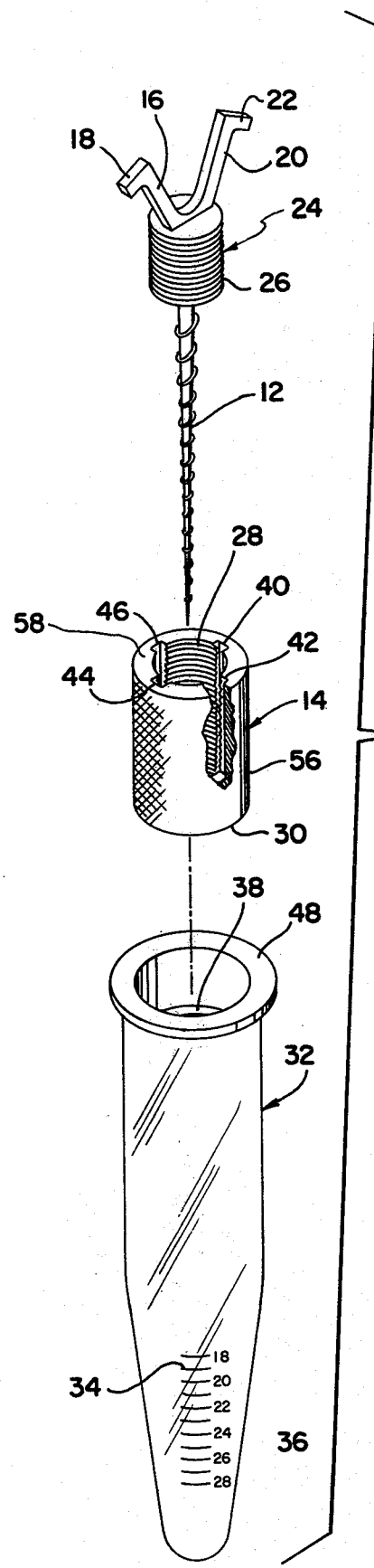
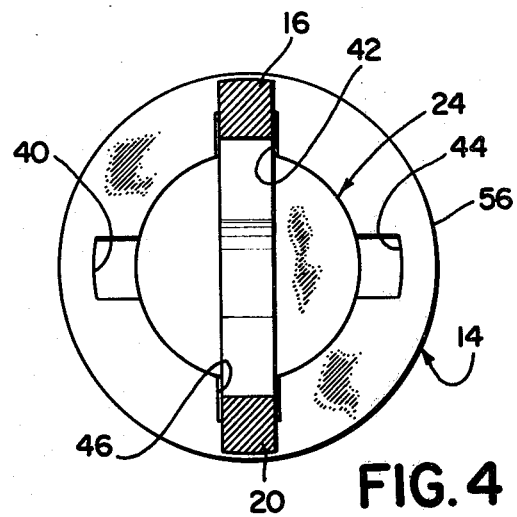
FIG. 4
FIG. 3
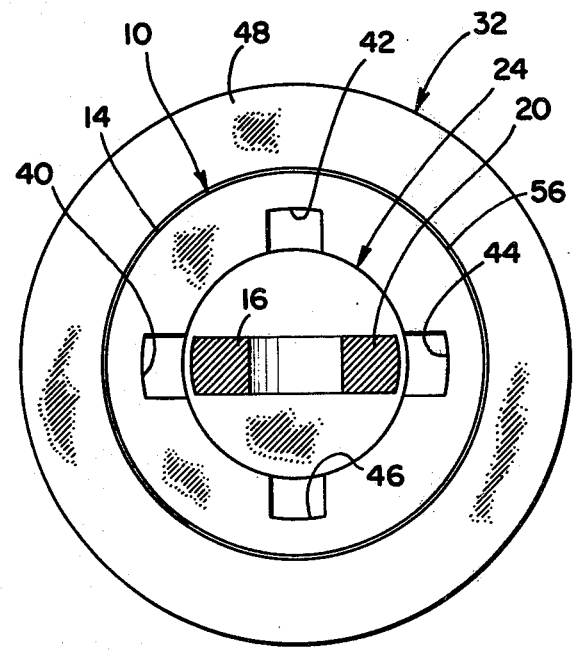
FIG. 5

PRECISION ENDODONTIC FILE

BACKGROUND OF THE INVENTION

The invention relates generally to the field of dental instruments, and more particularly, is directed to an improved, precision, endodontic file.

In the preparation of root canals, it is the present practice to enter the chamber of the tooth with a file or reamer to enlarge the root canal. A plurality of endodontic files or reamers of increasing diameter are employed to enlarge the root canal to create a channel of size that can practically be filled with a medicament and then sealed. It is important in the preparation of the root canal to control the length of the file in order to limit the depth of penetration to avoid injury. The current technique for forming this channel to the desired depth usually includes adjusting the length of the file by utilizing an x-ray of the tooth. A simple rubber marker or stopper that is movably positioned on the file has been employed to indicate on the file the depth disclosed by the x-ray. In this manner, when the file enters the root canal, the dentist can limit the depth of file insertion by observing the contact of the rubber marker at the edge of the tooth.

The problems with this prior art procedure are numerous. Firstly, it is difficult for the endodontist to precisely judge when the rubber stopper has reached the end of the tooth. Additionally, the rubber stopper is both flexible and movable and can therefore allow the file to proceed deeper into the root canal then may be actually desired. In other instances, the inadequacies of the equipment result in incomplete penetration. Either too great or too shallow depth penetration could cause failure of the entire procedure. An additional problem is presented in that each individual file and its rubber stopper must be separately gauged against a separate scale or ruler and then individually set to the depth indicated in the x-ray. This procedure can involve inherent inaccuracies and a great deal of time and inconvenience to the dentist. Inaccuracies can also occur because of the number of manual operations involved. Further, problems relating to contamination of the file during this measurement or gauging procedure are likely to occur.

It should be noted that errors in depth penetration of the file or reamer into the root canal, either too deep or too shallow, are the major cause of failure in endodontic procedures. In seeking to overcome such failure, the prior art endodontic instruments have been largely unsuccessful because of complexity or impracticability. Some devices developed by prior workers in the art have included excessive amounts of related paraphernalia or have been inordinately expensive in manufacture. Others have proven impracticable in manufacture or have been deficient in locking the devices or in complexity in calibration. Further, none of the devices currently available offer any assurity of maintaining sterility.

SUMMARY OF THE INVENTION

The present invention relates generally to a precision endodontic file and more particularly, is directed to an integral system for precisely determining the effective length of an endodontic file and for use of the same.

The present invention comprises an endodontic file which extends from a threaded base and a threaded collar, which collar also serves as a stop to prevent additional depth penetration to the root canal when the file is in use. The threaded base threadedly engages the collar whereby by rotating one part relative to the other, the position of the bottom of the collar can be precisely adjusted relative to the longitudinal extent of the tip or end of the file. Once the relative adjustable position of the base and collar has been preset the parts provide a positive stop against the edge of the tooth whereby the file cannot proceed into the root canal to a greater depth than that predetermined and preset upon the instrument.

The invention further comprises a cover that may preferably be fabricated of clear plastic material such as polyethylene plastic or polypropylene plastic upon which a plurality of graduation or scale markings may be imprinted in a well known manner. The cover includes an integral shoulder which receives and positions the bottom of the collar. By then scaling or measuring the desired depth penetration of the file into the root canal on a separate x-ray of a tooth, the dentist can set the precise depth on the instrument. The distance that the end of the file extends beyond the bottom of the collar is easily adjusted by turning the collar relative to the file to effect length adjustment provided by the threaded interconnection. By fabricating the cover of clear plastic, the tip or end of the file can be readily viewed therethrough in a manner to permit precise alignment of the bottom of the file with the desired scale graduation. In this manner, the depth of file penetration can be accurately set to any predetermined distance whereby the bottom of the file will be prevented from entering the tooth any further than desired.

It is noteworthy that the file will be kept sterile at all times inasmuch as the file will be protected by the cover during all length adjustment procedures. Once the desired length has been preset, the cover can be removed and disposed of, thereby leaving the instrument sterile, preset and ready for the work. In this manner, the previous inconvenience and time consuming operations of first measuring an x-ray of the tooth, and then by utilizing a ruler or scale, comparing the length of the file and its movable rubber stop on numerous occasions can be greatly simplified and speeded. By threadedly turning the collar relative to the file for length adjustment, and by viewing the file directly through the cover, the entire procedure is greatly simplified and rendered clinically more effective in that root canal puncture is effectively prevented.

In an interesting embodiment, the rear end of the threaded file body can be provided with one or more rearwardly extending spring arms which are normally biased radially outwardly. The rearward end of the threaded collar can be provided with one or more peripherally spaced slots into which the spring arms can be biased at various peripheral locations about the interior periphery of the rear of the collar. Once the exact desired longitudinal position of the bottom or end of the file is achieved by utilizing the graduations provided on the removable cover, the threaded base of the file can be locked in the desired longitudinal position along the threaded interior bore of the collar by releasing the spring arm or arms to fit within the indentations or slots provided at the rear of the collar.

In order to threadedly adjust the position of the file with respect to the collar, the spring arm or arms must be first squeezed radially inwardly so as not to engage a collar slot, thereby to permit the threaded adjustment.

Merely releasing then the spring arm or arms will lock the arms in an indentation or slot so that inadvertent relative movement of the reamer or file and the threaded collar will be absolutely prevented. In this manner, the lock acts to positively prevent any unwanted elongation of the file after the desired adjustment has been set. By utilizing the lock adjustment feature, the dentist can be assured that the end of the file will absolutely be prevented from accidently protruding through the end of the tooth root canal, which would thereby ruin the procedure.

As herein employed, the terms "file" and "reamer" have been interchangeably used to generally designate all instruments designed and utilized for penetration into the tooth root canal.

The present invention includes a precision endodontic file with accurate length adjustment means and incorporates positive mechanical stop means designed to insure against both over extension and under extension of file penetration. The integration of the scale graduations with the cover provides more accurate calibration and substantially eliminates errors in length adjustment.

The file construction enables accurate and rapid adjustment, thereby shortening patient chair time to thus contribute to patient comfort and well-being. By allowing a stable setting of file lengths, the device permits the dentist to operate in a manner which frees him of the concern of the possibility of over or under extension of files and reamers during the mechanical preparation of the root canal. The device enables the dentist to operate more rapidly and efficiently by removing the need to constantly compare the file calibration to insure that the settings have not become inadvertently miscalibrated during the mechanical procedures owing to the stable locking means embodied in the instrument.

The cover functions to insure that the device is at all times kept clean and sterile owing to the calibration cap which also serves to protect the file from inadvertently contacting contaminating surfaces during all manipulations prior to insertion into the root canal. In this manner, the incidence of infection to the patient can be considerably lowered.

It is therefore an object of the present invention to provide an improved, precision, endodontic file of the type set forth.

It is another object of the present invention to provide a novel precision endodontic file including an integral file and threaded base and a threaded collar which is longitudinally adjustable relative to the base.

It is another object of the present invention to provide a novel precision endodontic file incorporating length adjustment means and means to limit penetration of the file into a tooth root canal.

It is another object of the present invention to provide a novel precision endodontic file comprising in combination a file having a threaded, integral base, a threaded collar longitudinally adjustable relative to the base, the bottom of the collar providing a positive stop against the surface of the tooth to limit the depth of file penetration and means to lock the relative positions of the file and the collar after the desired penetration depth has been preset.

It is another object of the present invention to provide a novel precision endodontic file comprising a file having an integral threaded base, a collar threadedly adjustable relative to the base and a clear plastic cover overfitting the file and removable affixing to the collar whereby the file can be kept sterile during the length adjustment procedures.

It is another object of the present invention to provide a novel precision endodontic file comprising in combination an integral file and threaded base, a threaded collar longitudinally adjustable relative to the base to adjust the distance that the bottom of the file extends from the bottom of the collar and cover means overfitting the file and removably attaching to the collar, the cover means being provided with scale graduations and means to view the file visually therethrough to adjust the length of the file by aligning the bottom or end of the file with a desired one of the scale graduation markings.

It is another object of the present invention to provide a novel precision endodontic file that is adjustable in length without requiring extrinsic measuring devices.

It is another object of the present invention to provide a novel precision endodontic file comprising construction features allowing rapid, accurate, stable and sterile length calibration procedures.

It is another object of the present invention to provide a novel precision endodontic file that is inexpensive in manufacture, simple in design and trouble free when in use.

Other objects and a fuller understanding of the present invention will be had by referring to the attached specification and claims of a preferred embodiment thereof taken in conjunction with the accompanying drawings wherein like reference characters throughout designate similar parts and in which:

BRIEF DESCRIPTION OF THE DRAWINGS

FIG. 3 is an exploded, isometric view of the invention on reduced scale.

FIG. 4 is a cross sectional view taken along line 4—4 of FIG. 1, looking in the direction of the arrows.

FIG. 5 is a cross sectional view taken along line 5—5 of FIG. 2, looking in the direction of the arrows.

DESCRIPTION OF THE PREFERRED EMBODIMENT OF THE INVENTION

Figure 1:
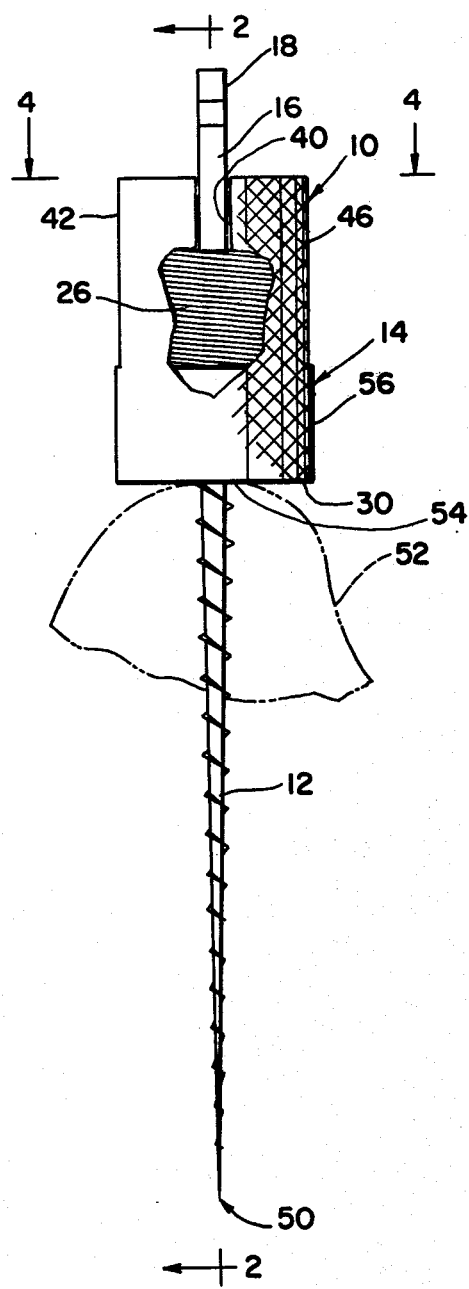
FIG. 1 is an elevational view of the precision endodontic file of the present invention, partially broken away, with a portion of a tooth being illustrated in phantom lines for purposes of association.

Although specific terms are used in the following description for the sake of clarity, these terms are intended to refer only to the particular structure of my invention selected for illustration in the drawings and are not intended to define or limit the scope of the invention.

Figure 2:
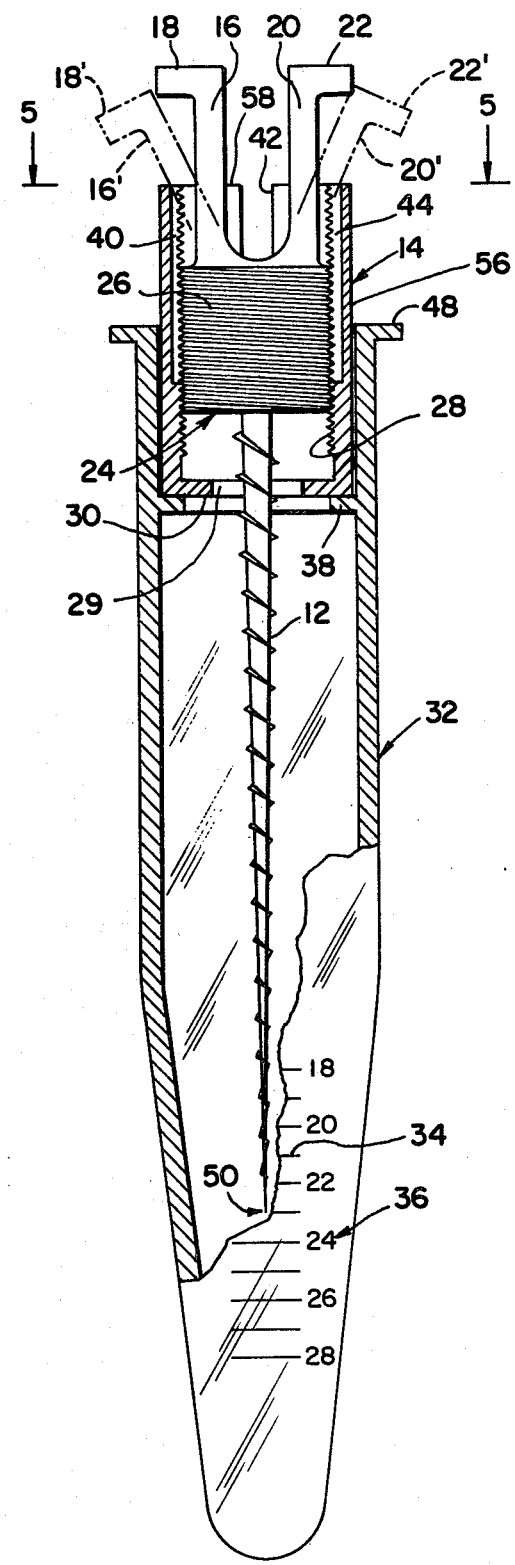
FIG. 2 is a cross sectional view taken along line 2—2 of FIG. 1 looking in the direction of the arrows, with the cover added and partly broken away and partly in section to illustrate interior construction details. The adjusting handles are illustrated in full lines in the adjustment position and in phantom lines in the locked position.

Referring now to the drawings, there is illustrated in FIGS. 1, 2 and 3 a precision endodontic file 10 constructed in accordance with the teachings of the present invention. As illustrated, the invention comprises generally a file or reamer 12 of the usual configuration and construction of a conventional endodontic file. The file 12 projects from and may be integrally formed with a base 24, which is provided with an externally threaded periphery. Preferably, the pitch of the thread 26 is small to permit precise length adjustment of the file 12 relative to the collar or sleeve 14 as hereinafter more fully set forth. The file base 24 may be fabricated of metal plastic of suitable properties to be machined, molded or otherwise treated to provide the threaded periphery 26.

A collar or sleeve 14, which also may be of metal or plastic suitable to be treated to provide a threaded interior bore 28, overfits and threadedly receives the needle base 24 therewithin. It is the essence of this invention that the length of the reamer or file 12 can be adjustable relative to the sleeve 14 by turning the base 24 relative to the sleeve 14 to thereby vary the distance between the reamer or file tip 50 and the collar bottom or stop 30. Preferably the outer peripheral surface of the collar is serrated or otherwise roughened to provide a non-slip grasping surface to facilitate manipulation of the instrument.

The file base 24 terminates rearwardly or upwardly in one or more rearwardly extending adjusting handles 16, 20 which may be provided with radially outwardly projecting grips 18, 22 if so desired to facilitate file length adjustment. In the preferred embodiment, the adjusting handle or handles 16, 20 are provided with means to normally bias the handles radially outwardly for locking purposes after the desired length adjustment has been made. As illustrated in full lines in FIG. 2, the adjusting handles 16, 20 are shown in their adjusting positions whereby the handles have been squeezed together radially inwardly to clear the threads 28 of the collar or sleeve 14 against the outwardly biasing means. In this position it will be observed that the threaded base 24 can be turned relative to the threaded bore 28 of the sleeve to thereby longitudinally adjust the position of the base (and the projecting file 12) relative to the collar 14. When the desired length adjustment has been achieved, the grips 18, 20 can be released, thereby permitting the adjusting handles 16, 20 to bias radially outwardly to the locked position as illustrated in dotted lines in FIG. 2 to the positions designated respectively 16', 18' and 20', 22'. As seen in FIG. 1, once the desired length adjustment has been made, the instrument 10 can be employed by inserting the file 12 into the root canal (not illustrated) of a tooth 52 until the bottom 30 of the sleeve 14 contacts and stops upon the proximate surface 54 of the tooth crown 52. In this manner, the precise depth of penetration of the tip 50 of the file 12 within the root canal of the tooth 52 can be precisely determined and limited.

Referring now to FIGS. 2 and 3, it will be observed that the end of the sleeve 14 remote from the direction of tooth penetration can be machined or otherwise treated to provide locking means which may be in the form of one or more slots 40, 42, 44, 46 which extend radially outwardly from the threaded periphery of the sleeve bore 29. In this preferred embodiment, the slots 40, 42, 44, 46 are arranged in opposed pairs wherein each slot of the pair is diametrically opposed and wherein the pairs are positioned at diametrical right angles. Thus, one slot is provided every ninety degrees about the circumference of the collar bore 29. In the preferred embodiment as illustrated, the slots 40, 42, 44, 46 project radially outwardly from the sleeve bore 29 approximately one half of the thickness of the sleeve sidewall and do not extend completely through the outer periphery 56. Preferably, the slots extend downwardly from the remote end 58 and terminate short of the sleeve bottom or stop surface 30. In the preferred embodiment, the slots 40, 42, 44, 46 extend from the remote sleeve end 58 towards the stop end 30 approximately two-thirds of the distance, thereby to facilitate a wide range of length adjustment of the file 12 relative to the sleeve and to provide adequate locking facilities at all adjusted longitudinal positions of the threaded base 24 within the sleeve threaded bore 28. The locking means should securely interconnect the base 24 and the sleeve 14 to allow both rotative movement and longitudinal movement of the parts as the instrument is calibrated.

In order to adjust the distance the file tip 50 extends beyond the sleeve stop surface 30, a respective handle or handles 16, 20 can be grasped by the fingers of the dentist at the grip portions 18, 22 and squeezed radially inwardly against the bias means continuously urging the handles 16, 20 apart. See FIG. 2. By squeezing the adjusting handles radially inwardly the handles 16, 20 will be positioned entirely within the sleeve bore 29 and fully clear of contact with either the periphery of the threaded bore or contact within any of the slots 40, 42, 44, 46. With the parts positioned as illustrated in full lines in FIG. 2, the collar 14 can be turned relative to the threaded base 24 to thereby longitudinally adjust the position of the file tip 50 relative to the bottom surface or stop surface 30 of the threaded collar 14.

In use, an x-ray of the tooth 52 is taken in conventional manner to determine the relative position and depth of the tooth root canal (not illustrated). Then by measuring the x-ray with a conventional scale or rule, the precise, desired depth of file penetration into the tooth 52 can be determined. With the length adjustment thus determined, the parts can be arranged as illustrated in FIG. 2 and the file base 24 can be longitudinally adjusted within the threaded collar as desired. In this procedure, the precise distance between the file tip 50 and the bottom 30 of the collar can be determined by sighting through the transparent sidewalls of the cover 32 until the tip 50 aligns with a desired cover graduation 34 as indicated by the scale indicia 36. The cover 32 includes an integral, internal flange 38 which acts as a seat to receive and precisely position the collar bottom 30 during the file length adjustment procedures. Once the precise length adjustment has been accomplished, the adjusting handles 16, 20 can be released from the positions illustrated in FIGS. 2 and 5. The spring means built into the adjusting handle will function automatically to bias the adjusting handles radially outwardly to the positions indicated in dotted lines in FIG. 2, namely 16', 20'. When the adjusting handles 16, 20 do not position naturally within one or more of the collar slots 40, 42, 44, 46, the collar can be rotated slightly relative to the base in either clockwise or counterclockwise direction until the parts lock together. Once the adjusting handles 16, 20 are locked within one or more of the collar slots, the cover 32 can be grasped at the body or at the annular flange 48 to remove completely the cover 32 from association with the sleeve 14, thereby exposing the file 12 for the desired procedures. It will be noted that the file 12 has been maintained covered and in sterile condition throughout the entire length adjusting operations.

In the preferred embodiment, it is contemplated that the length of the sleeve 14 will be approximately 10½ mm. overall, and that the slots 40, 42, 44, 46 will extend from the remote end 58 toward the stop end 30 a distance approximately 6½ mm. Preferably, the threaded base 24 will extend in length approximately 5 mm. and the adjusting handles 16, 20 will rise from the remote end of the base 24 a distance of aproximately 7 mm. In order to accommodate the usual depth of most teeth, it is contemplated to provide files 12 of three standard lengths in addition to the usual diametrical variations (which may number as many as sixteen in a conventional complete set). It is preferred to provide one standard file length of 28 mm., one standard file length of 24½ mm., and one standard file length of 21 mm. Thus, a complete set for use with substantially all size teeth normally encountered by a dentist could comprise a set of variable diameter files of 28 mm. length, a set of 16 variable diameter files of 24½ mm. length and a set of 16 variable diameter files of 21 mm. length. A single collar or sleeve 14 and a single calibration cover would be usable with all of the files. In this manner, the 28 mm. files would be adjustable over a range of approximately 24 mm. to 28 mm. The 24½ mm. files would be adjustable over a range of approximately of 20½ mm. to 24½ mm. and the 21 mm. files would be adjustable over a range from approximately 17 mm. to approximately 21 mm.

Although the present invention has been described with a reference to the particular embodiments herein set forth, it is understood that the present disclosure has been made only by way of example and that numerous changes in the details of construction may be resorted to without departing from the spirit and scope of the invention. Thus, the scope of the invention should not be limited by the foregoing specification, but rather only by the scope of the claims appended hereto.

What is claimed is:

1. A precision endodontic file, comprising:
   sleeve means;
   base means disposed in said sleeve means;
   means for adjusting the relative position of said sleeve means and said base means, the adjustment means including locking means;
   an endodontic file affixed to said base means and extending beyond said sleeve means; and,
   cover means positively and removably engaging said sleeve means and overfitting said file, said cover means including scale means for directly adjusting the extension of said file beyond said sleeve means, prior to removal of said cover and use of said file.

2. The endodontic file of claim 1 wherein the adjustment means comprises mating threaded sections.

3. The endodontic file of claim 2 wherein the sleeve means comprises a longitudinal bore.

4. The precision endodontic file of claim 3 wherein one of the threaded sections is formed along the longitudinal bore and another of the threaded sections is formed on a corresponding surface of the base means.

5. The endodontic file of claim 1 wherein the cover means is adapted to maintain the file in protected condition.

6. The endodontic file of claim 1 wherein the locking means positively interengage to the sleeve means and the base means in any selected relative position.

7. The precision endodontic file of claim 6 wherein the locking means comprises at least one adjustment handle to adjust the relative position of the base means and the sleeve means.

8. The endodontic file of claim 7 wherein the at least one adjustment handle comprises means to continuously bias the at least one handle outwardly.

9. The endodontic file of claim 8 wherein the outward direction is radially outwardly.

10. The endodontic file of claim 7 wherein the locking means further comprises at least one slot, the at least one adjustment handle being adapted to releasably engage the at least one slot to prevent relative rotational movement between the sleeve means and the base means.

11. The endodontic file of claim 10 wherein said at least one slot is formed in the sleeve means.

12. The endodontic file of claim 11 wherein the sleeve means comprises a longitudinal bore and the at least one slot is formed in the bore.

13. The endodontic file of claim 7 wherein said at least one handle extends from said base means.

14. The precision endodontic file of claim 1 wherein the sleeve means comprises slot means into which a handle can be biased to prevent relative movement between the sleeve means and the base means.

15. The precision endodontic file of claim 1 wherein the cover means is fabricated of transparent material.

16. The precision endodontic file of claim 15 wherein the cover means includes a plurality of scale graduations.

17. The precision endodontic file of claim 16 wherein the cover means is adapted to permit the adjustable extension of the file in accordance with the scale graduations.

18. The precision endodontic file of claim 1 wherein the cover means comprises shoulder means to receive the sleeve means to precisely position the cover means relative to the sleeve means.

19. The precision endodontic file of claim 18 wherein the sleeve means comprises a bottom surface, said bottom surface providing a stop to limit penetration of the file into a tooth.

20. The precision endodontic file of claim 18 wherein the shoulder means comprises an annular shoulder.

21. The precision endodontic file of claim 20 wherein the bottom surface contacts the annular shoulder.

* * * * *